United States Patent [19]

Tazuma et al.

[11] Patent Number: 4,462,968

[45] Date of Patent: Jul. 31, 1984

[54] FINISHING PROCESS FOR THE REMOVAL OF SULFUR COMPOUNDS FROM A GAS STREAM

[75] Inventors: James J. Tazuma, Stow; Kenneth J. Frech, Tallmadge, both of Ohio

[73] Assignee: The Goodyear Tire & Rubber Company, Akron, Ohio

[21] Appl. No.: 410,186

[22] Filed: Aug. 23, 1982

[51] Int. Cl.$^3$ .............................................. B01D 53/34
[52] U.S. Cl. .................................. 423/224; 423/228; 423/229; 423/232; 423/234; 423/242; 423/243
[58] Field of Search ............... 423/243, 242 A, 242 R, 423/224, 228, 229, 234, 232

[56] References Cited

FOREIGN PATENT DOCUMENTS

| | | | |
|---|---|---|---|
| 49-105775 | 10/1974 | Japan | 423/224 |
| 53-58480 | 5/1978 | Japan | 423/224 |
| 1130127 | 10/1968 | United Kingdom | 423/224 |

*Primary Examiner*—Earl C. Thomas
*Assistant Examiner*—Jeffrey E. Russel
*Attorney, Agent, or Firm*—D. O. Nickey

[57] ABSTRACT

The invention relates to a finishing process for the removal of low level concentrations of mercaptans, sulfides and disulfides from a gas stream, especially a natural gas stream. The sulfur compounds are washed from the gas stream with a solution containing hydrogen peroxide, sodium carbonate or sodium hydroxide, and ammonia or an amine.

2 Claims, No Drawings

FINISHING PROCESS FOR THE REMOVAL OF SULFUR COMPOUNDS FROM A GAS STREAM

RELATED APPLICATION

The process of this invention is similar to a process described in U.S. patent application Ser. No. 352,812, now U.S. Pat. No. 4,435,371.

TECHNICAL FIELD

A process has been developed for the removal of mercaptans and organic sulfides from a gas stream, more specifically, a natural gas stream. The present invention provides a process for the nearly total removal of sulfur compounds from a gas stream.

BACKGROUND ART

Removal of sulfur compounds from gas streams has been of considerable importance in the past and is even more so today due to environmental considerations. Gas effluent from the combustion of organic materials, such as coal, almost always contains sulfur compounds and sulfur removal processes have concentrated on removing hydrogen sulfide since it has been determined to be a significant health hazard. With increasing emphasis on the elimination of sulfur discharge to the atmosphere and the utilization of natural gas streams that were heretofore unusable due to their sulfur content, attention is turning to the removal of sulfur compounds from gas streams.

The process of the present invention provides a finishing means for the removal of low level concentrations of mercaptans, sulfides and disulfides from a gas stream, specifically natural gas.

Numerous natural gas wells produce what is called in the industry "sour gas." Sour gas is natural gas that contains hydrogen sulfide, mercaptans, sulfides and disulfides in concentrations that make its use unacceptable. Considerable effort has been expended to find an effective and cost efficient means to remove these objectionable sulfur compounds from natural gas. The commercially available processes for the desulfurization of natural gas have been primarily concerned with the removal of hydrogen sulfide. At present the interstate pipeline system for natural gas has a limit of one-quarter gram or 4 ppm of hydrogen sulfide. This can usually be obtained by the use of alkanol amine, iron sponge and zinc compound processes. However, none of these processes are suitable or effective for treatment of natural gas containing low levels of mercaptans, sulfides and disulfides.

U.S. Pat. No. 4,283,373 by the present inventors discloses a process which consists of contacting a gas stream with alkali metal salts of sulfonamides or resins containing sulfinamide functionalities in the presence of an iron sponge bed. Further, U.S. Pat. No. 4,311,680 discloses a process wherein an iron sponge bed is enhanced through the use of hydrogen peroxide. These processes and others contained in U.S. Pat. Nos. 632,400, 1,934,242, 4,027,002, 4,238,463 and 4,278,646 all describe processes resulting in the removal of most of the hydrogen sulfide. Some work has demonstrated that some of the mercaptans, as well as some of the sulfides and disulfides and residual sulfides are removed. However, these processes do not meet the more severe demands placed on special uses of natural gas or gas streams where lower sulfur levels are required.

A very pure natural gas is required for foundry applications wherein metals susceptible to sulfur poisoning or degradation are melted or alloyed. Specifically, furnaces which melt aluminum alloys require extremely low sulfur gas since the sulfur compounds react with aluminum. Aluminum alloys can be directly fired by natural gas in graphite crucibles; however, the graphite crucible is porous to gases so that the molten aluminum alloy absorbs sulfur compounds which are converted to aluminum sulfide. The presence of this sulfide adversely affects the alloy so that poor molds are obtained. Thus, it has been found desirable to reduce total sulfur to 1 to 6 ppm level in the natural gas.

There is a present need for an efficient low cost finishing process which will essentially remove all of the mercaptans, sulfides and disulfides from a gas stream.

All the references cited do not suggest or disclose a process for the removal of mercaptans, sulfides, disulfides and residual sulfides from a gas stream through the use of a scrubbing solution which consists of hydrogen peroxide alone or in combination with ammonia or an amine.

DISCLOSURE OF THE INVENTION

There is disclosed a process for removing mercaptans, sulfides, disulfides and residual sulfides from a gas stream that is essentially free of hydrogen sulfide which consists of contacting said gas stream with a solution containing ammonia or an amine and hydrogen peroxide. Further, there is disclosed a process for the removal of sulfur compounds from a gas stream which comprises contacting said gas stream with a solution consisting of (a) 1 to 25 percent by weight hydrogen peroxide, (b) 1 to 15 percent by weight of sodium carbonate or sodium hydroxide; (c) 1 percent by weight to saturation of ammonia or an amine, and (d) 1 to 5 percent by weight sodium silicate.

The process of the present invention can be carried out in single or multi-stage operations. Single stage operation is preferred for natural gas with sulfur levels of 10 to 50 ppm, consisting of sulfur compounds other than $H_2S$. For natural gas containing large amounts of $H_2S$ a preferred process would consist of a first unit which would remove most of the $H_2S$. For gases containing larger amounts of $H_2S$ the alkanol amine scrubber is recommended and for lesser amounts an iron sponge bed continuously regenerated with hydrogen peroxide is preferred. The remaining mercaptans, sulfides and disulfides are then removed in a second unit which contains a scrubbing solution which consists of hydrogen peroxide alone or in combination with ammonia or an amine.

The treatment unit or scrubber is fabricated from any material which is inert to hydrogen peroxide and ammonia or the amine, such as aluminum or a polyolefin coated vessel. The scrubber is designed so as to provide a fine dispersion of bubbles through the peroxide/amine or ammonia solution, i.e. the scrubber can be fitted with distributor plates or more conveniently filled with a packing such as berl saddles, polyethylene cylinders, vermiculite, or aluminum protruded packing. It would be obvious to a skilled chemical engineer that numerous devices would be appropriate for use of the present invention. The requirement is that the gas stream to be treated have sufficient contact with the treatment solution so as to effect economical, efficient, and almost total removal of mercaptans, sulfides, disulfides and residual sulfides from the gas stream. Further, the scrubber filled with the peroxide/amine or ammonia solution can have the gas passed upwards through the solution or it can be a trickle bed type system in which the hydrogen peroxide/amine or ammonia solution flows downward through the treatment vessel with the gas flow in the same or opposite direction.

Another means for contacting the gas stream with the scrubber solution consists of a spray dispersion of the solution into the gas stream. This is accomplished by the scrubbing solution being sprayed under pressure into a treatment vessel through which the sour gas is passing. The liquid is collected at the bottom of the treatment vessel and either rejuvenated and recirculated to the treatment vessel or discarded.

The treatment solution which contains hydrogen peroxide and ammonia or an amine can contain hydrogen peroxide at a concentration that can be varied over a wide range, with the preferred range being 3 to 25 percent $H_2O_2$ by weight. A more preferred concentration of the hydrogen peroxide is 10 to 25 percent by weight. It has been found that a scrubber solution of hydrogen peroxide/amine or ammonia is most preferred. This solution has been more effective than hydrogen peroxide solution alone in removing the more refractory sulfur compounds whose chemical structure is not known. The hydrogen peroxide/amine or ammonia mixture is, however, less stable. The half-life for $H_2O_2$ in a 0.8 molar ammonium hydroxide 0.2 molar peroxide solution was 40 hours at room temperature. This suggests that an operation where small amounts of ammonium hydroxide and $H_2O_2$ solution are constantly and individually added to the treatment unit would be the optimum method of operation.

It has been found that the hydrogen peroxide/amine or ammonia scrubbing solution may be advantageously stabilized through the addition of 1.0 to 5.0 percent by weight sodium silicate to total solution.

Representative of other oxidizing agents that may be useful in the process of the present invention are tert-dibutyl peroxide, t-butyl hydroperoxide, cumene hydroperoxide, dicumyl peroxide and other commercially available organic peroxides and hydroperoxides. The most preferred oxidizing agent is hydrogen peroxide.

Representative of the amines that are useful in the process of the present invention are methyl amine, dimethyl amine, ethyl amine, diethyl amine, ethanol amine, diethanol amine, propanol amine and dipropanol amine. Preferred amines are methyl amine, dimethyl amine, trimethyl amine and diethanol amine. Ammonia is more preferred than the amines.

The amine in the scrubbing solution may be anhydrous, aqueous solutions of the amine or water/alcohol solutions of the amine. Alcohols of 1 to 4 carbon atoms are useful in preparing the water/alcohol amine solutions. Such alcohols include methanol, ethanol, propanol, isopropanol, butanol and isobutanol.

The concentration of ammonia or the amine in the scrubbing solution bed is preferably high. It has been found that concentrations of 0.2 Normal to saturated solutions are appropriate for a batch-type; however, the more concentrated solutions are preferred. In fact, the addition of anhydrous ammonia or anhydrous amines is advantageous since lower concentrations only result in the unnecessary addition of liquid material to the treatment vessel which eventually has to be removed.

The use of the alcohol cosolvent in the preparation of the scrubbing solution is only required when the amines have limited water solubility. Only when the amine has limited water solubility should the alcohol cosolvent be used.

To one skilled in chemistry it is readily apparent that anhydrous amines, and anhydrous ammonia, will, when placed in an aqueous media, form the hydrates thereof, i.e., ammonium hydroxide as well as aqueous ammonia. The process of the present invention contemplates these hydrates and has found the use of ammonia dissolved in water to be especially useful.

The applicants have found that the use of a caustic solution will enhance the process of the present invention. Aqueous solutions of NaOH, KOH and $Na_2CO_3$ have been found to be appropriate.

The process of the present invention may be conducted on a continuous basis or batch type. In the total batch type operation the fluid-filler reactor is operated until the scrubbing solution is no longer effective and is then replaced by fresh scrubbing solution. In continuous operation a rate of addition of hydrogen peroxide and ammonia or amine is established to effect the desired removal of sulfur compounds while exhausted solution containing flocculent sulfur is discharged from the reactor. Further, the hydrogen peroxide may be continuously added to the solution with only intermittent addition of ammonia or the amine. This is preferred since the hydrogen peroxide decomposes during the reaction while the amine and ammonia do not.

The amine or ammonia in either anhydrous or hydrated form may be metered in the gas stream prior to entry into the peroxide solution containing reactor.

BEST MODE FOR CARRYING OUT THE INVENTION

The process of the present invention was demonstrated using a cylindrical glass reactor measuring 4 inches (10.16 cm) by 48 inches (121.9 cm) fitted with metal plates clamped at either end to which were attached the inlet and outlet connections. The gas flow was metered at 27 psig ($\approx 186$ kPa) with a Brooks pressure rotometer unit which measured flow between 200 cc per minute and 1.2 liters per minute under standard conditions. The glass reactor was filled with quarter-inch, half moon, ceramic saddles, available from the Norton Company, with a void space of approximately 4.8 liters for the scrubber solution.

The process of the present invention was utilized on a sour natural gas well from the Newburg formation of Ohio. The well-head analysis of the sour gas was as follows:

| Compound | ppm by wt |
| --- | --- |
| $H_2S$ | 134.4 |
| $CH_3SH$ | 2.1 |
| $C_2H_5SH$ | 16.9 |
| $C_4H_9SH$ | 5.9 |
| $C_5H_{11}SH$ | 1.7 |
| Sulfides | 12.9 |
| Residual sulfides | 0.2 |

The natural gas prior to treatment by the process of the present invention was first contacted with an iron sponge treater so as to essentially remove all the $H_2S$. The analysis of the gas stream after passing through the iron sponge treater analyzed by a Barton Titrator measured 22 ppm sulfur by weight. This 22 ppm sulfur by weight consisted of about 8 to 10 ppm of sulfides and disulfides and 12 to 14 ppm of mixed mercaptans. Passage of this prior treated gas through 4.7 liters of 3 percent $H_2O_2$ (0.88 molar) at a gas flow rate of 340 cc per minute (standard) lowered the sulfur level to 3 ppm. When the scrubbing solution was changed to 0.88 molar $H_2O_2$ (3 percent) and 2.4 molar $NH_4OH$ and a gas flow of 340 cc per minute the total sulfur content was reduced to about 1 ppm.

EXAMPLES 1 THROUGH 6

The treatment vessel was as described above, however, the flow rate and concentration of the peroxide and ammonium hydroxide were varied in the following examples. The temperature of the reaction was ambient temperature. Table I sets out the results and variables for Examples 1 through 6.

TABLE I

| Example No. | Scrubber Solution | Gas Flow Rate | Inlet S-Content ppm | Outlet S-Content ppm |
|---|---|---|---|---|
| 1 | 3% $H_2O_2$ (0.88 M) 4.9 l | 360 cc/min | 22 | 3 |
| 2 | 3% $H_2O_2$ (0.88 M) 3.4 M $NH_4OH$ 4.7 l | 360 cc/min | 22 | 1 |
| 3. | 11.5% $H_2O_2$ (3.4 M) 4.2 l | 890 cc/min | 26 | 2 |
| 4. | 11.5% $H_2O_2$ (3.4 M) 4.2 l | 935 cc/min | 32 | 2 |
| 5. | 11.5% $H_2O_2$ 1 liter | 1.2 l/min | 27 | 2 |
| 6. | 11.5% $H_2O_2$ | 1.2 l/min | 28 | 2 |

EXAMPLES 7 THROUGH 13

The process of the present invention was also used on a natural gas well which is produced from the Clinton formation of Ohio. This gas contained approximately 18 ppm of unknown sulfur compounds. In addition this gas had been previously treated to remove essentially all of the $H_2S$. The treatment vessel and procedure were as described in Examples 1 through 6, however, the scrubbing solution, the flow rate and the concentration of the scrubbing solution were varied.

Table II sets out the variables with the results.

TABLE II

| Example No. | Scrubber Solution (Total Volume) | Gas Flow Rate | Inlet S-Content ppm | Outlet S-Content ppm |
|---|---|---|---|---|
| 7 | 11.5% $H_2O_2$ (4.2 l) | 650 cc/min | 18 | 11 |
| 8 | 11.5% $H_2O_2$ (4.2 l) | 200 cc/min | 18 | 11 |
| 9 | 25% $H_2O_2$ (3.5 l) | 330 cc/min | 18 | 12 |
| 10 | 5% $Na_2CO_3$ 11.5% $H_2O_2$ (4.0 l) | 370 cc/min | 18 | 9 |
| 11 | 5% $Na_2CO_3$ 11.5% $H_2O_2$ (4.0 l) | 900 cc/min | 18 | 12 |
| 12 | 3.2 M $NH_4OH$ 3.4 M $H_2O_2$ (4.1 l) | 1.2 l/min | 18 | 12 |
| 13 | 3.2 M $NH_4OH$ 3.4 M $H_2O_2$ (4.1 l) | 500 cc/min | 18 | 6 |

From Table II it is evident that natural gas which contains 18 ppm by weight of sulfur compounds is made up of 7 ppm of sulfur compounds that are easily removed by $H_2O_2$. This indicates that the removed compounds are probably mercaptans and sulfides. The remainder about 11 ppm are more refractory sulfur compounds. About 2 ppm was further removed by using $Na_2CO_3$—$H_2O_2$ solution while an additional 5 ppm was removed with the $NH_4OH$—$H_2O_2$ scrubbing solution.

It is evident that the $NH_4OH$—$H_2O_2$ scrubbing solution is more effective than $Na_2CO_3$—$H_2O_2$ or $H_2O_2$ alone for the desulfurization of the gas stream.

INDUSTRIAL APPLICABILITY

The process of this invention which employs the use of hydrogen peroxide and ammonia or an amine has numerous industrial applications. The need for effective and economic means for finishing a gas stream which contains low level concentrations of sulfur compounds has been long felt. This invention will be useful in treating effluent from coke ovens, sewage plants, paper mills and in particular, sour natural gas streams, wherein the use of the natural gas requires extremely low levels of sulfur compounds.

While certain representative embodiments and details have been shown for the purpose of illustrating the invention, it will be apparent to those skilled in this art that various changes and modifications may be made therein without departing from the scope of the invention.

We claim:

1. A process for removing mercaptans, sulfides and disulfides from a natural gas stream that consists of contacting said natural gas stream with a solution consisting of (a) 1 to 25% hydrogen peroxide by weight (b) 1 to 15% by weight sodium carbonate or sodium hydroxide and (c) 1% by weight to saturation of ammonia.

2. A process for removing mercaptans, sulfides and disulfides from a natural gas stream that consists of contacting said natural gas stream with a solution consisting of (a) 1 to 25% hydrogen peroxide by weight (b) 1 to 15% by weight sodium carbonate or sodium hydroxide and (c) 1% by weight to saturation of an amine selected from the group consisting of methyl amine, ethanol amine and diethanol amine.

* * * * *